United States Patent [19]

Gay et al.

[11] 4,447,414
[45] May 8, 1984

[54] CARNIVORE ANTHELMINTICS

[75] Inventors: John C. Gay, St. Joseph, Mo.; H. Dennis McCurdy, Merriam; Wayne B. Rose, Overland Park, both of Kans.

[73] Assignee: Cutter Laboratories, Inc., Berkeley, Calif.

[21] Appl. No.: 451,990

[22] Filed: Dec. 21, 1982

[51] Int. Cl.$^3$ .................... A61K 31/78; A61K 31/495
[52] U.S. Cl. ........................................ 424/81; 424/78; 424/250; 424/258; 424/300
[58] Field of Search .................... 424/258, 78, 250, 81

[56] References Cited
PUBLICATIONS

Dorn et al.-Chem. Abst. vol. 93 (1980) p. 53996f.
Seubert et al.-Chem. Abst. vol. 84 (1976) p. 5007b.
Wikerhauser et al.-Chem. Abst. vol. 93 (1980) p. 61639g.

Primary Examiner—Sam Rosen
Attorney, Agent, or Firm—James A. Giblin

[57] ABSTRACT

A broad spectrum anthelmintic composition useful for eliminating nematodes and cestodes from carnivores. Composition comprises anthelmintically effective amounts of compounds which act systemically and via direct contact in carnivore gut, the compounds being carried in a vehicle which provides simultaneous systemic and direct contact availability of the compounds. Preferred composition comprises febantel and praziquantel compounds in an aqueous paste-like formulation.

16 Claims, No Drawings

CARNIVORE ANTHELMINTICS

BACKGROUND OF THE INVENTION

1. Field

This disclosure is concerned generally with anthelmintic preparations and specifically with a single, easy-to-administer preparation useful in eliminating common helminths including both nematodes and cestodes from carnivores, especially domesticated animals such as dogs and cats.

2. Prior Art

The term anthelmintics is used to describe a broad class of compounds useful for expelling or destroying parasitic worms, especially those found in the intestine. Depending of the specific anthelmintic compound, the action against the worms will be either primarily systemic or primarily via direct contact with the worms in the gastrointestinal tract of the afflicted animal. In general, the type of anthelmintic to be used will depend on the class or classes of worms to be eliminated.

In the case of larger animals such as cattle and horses, such anthelmintics have been simply mixed with the animals' feed ration in the form of a powder, granules, suspension or, more recently, as a paste which, due to its tacky nature, will adhere to the grain parts. Such tackiness not only assures that the anthelmintic will in fact be ingested by the animal, but also assures an anthelmintically effective direct contact with worms as the grain/anthelmintic paste passes through the gastrointestinal tract. Examples of such anthelmintic pastes can be found in U.S. Pat. No. 3,746,490 to Marsland et al (resin based formulation of the liquid dimethyl-2,2-dichlorovinyl phosphate or DDVP), U.S. Pat. No. 4,141,975 to Gay et al (mineral oil based formulation of trichlorfon) and U.S. Pat. No. 4,277,467 to Dorn et al (trichlorfon and febantel in a paste formulation having a water content of less than 1% by weight).

A broad spectrum anthelmintic for carnivores, unlike those developed for farm animals and horses, must concern itself with both nematode (roundworm) and cestode (flatworm or tapeworm) parasites. Cestodes have not routinely been perceived as a serious economic problem in food animals or of sufficient incidence in horses to warrant product development. These different classes of parasites have frequently required separate medications or combinations of medications to achieve their degree of success. These products in carnivores, especially domesticated dogs and cats, have all had their shortcomings. Vermiplex TM anthelmintic, like similar products from other manufacturers, is a combination oil-based capsule for dogs and cats. It is difficult to administer, particularly to cats, and is marginal in efficacy particularly with respect to cestodes. A paste product (Felex#) is available for cats in Australia, but its activity is limited to nematodes. For dogs, there is a powder formulation of mebendazole (Telmintic TM ) available, but it is essentially ineffective against *Dipylidium caninum,* a common cestode in dogs. Also, its efficacy is dependent on successful administration through mixing in the food.

Attempts to formulate a broad spectrum (i.e. covering all common nematodes and cestodes) yet easy-to-administer anthelmintic preparation for carnivores have been difficult and to date unsuccessful. To assure a broad spectrum action, it would apparently be necessary to somehow combine anthelmintics which are on the one hand primarily systemically active with, on the other hand, anthelmintics which are active against helminths primarily via direct contact in the carnivore gut (or gastrointestinal tract). In general, the best system for the base would be a formulation that would provide for maximum anthelmintic response of both the active components and also one in which both active ingredients were stable. The one agent, primarily systemic in nature, should be given in a form that is readily available for absorption from the gut into the carnivore blood stream. A systemically active anthelmintic known as praziquantel (DRONCIT ® anthelmintic, Bayvet Division, Cutter Laboratories, Inc., Shawnee, Kan.), is known to be effective against cestodes (tapeworms). See Kruckenberg, S. M. et al, "Preliminary Studies of the Effects of Praziquantel Against Tapeworms in Dogs and Cats", VM/SAC 77:689–692, 1981.

Among the anthelmintics known to be effective against worms via direct contact in the gut is febantel (see U.S. Pat. No. 3,993,682 to Kölling et al). In general, such anthelmintics do not dissolve completely in water and this partial insolubility and the poor absorption by the gastrointestinal tract tends to assure their direct-contact action against certain intestinal worms. Because of their limited solubility, such anthelmintics may be administered in the form of a suspension of fine particles or in a paste-like form which can be administered in the food. In paste applications, the particle size of the anthelmintic compound is commonly controlled to assist in paste formation (see U.S. Pat. No. 4,141,975 cited above) and in dispersion of particles in the formulation to assure anthelmintic activity. Other anthelmintic pastes are disclosed in an article by R. M. Corwin et al, Am. J. of Vet. Res., Vol. 43, No. 6, pp. 1100–1102, 1982 (febantel paste) and the articles cited therein (febantel/trichlorfon paste).

Since the direct-contact anthelmintics do not rely on water solubility for their administration, it has been common practice to use as a vehicle an inert organic liquid such as mineral oil to assist in particle dispersion, paste formation and product stability. Thus, water has been avoided or minimized in these products and, in the case of a recent combination paste of two anthelmintics (trichlorfon and febantel), it is a requirement that the water content, if any, be less than 1 percent by weight of the paste. Unfortunately, by limiting the water content (e.g. to assure long term stability), it becomes difficult to formulate certain water-soluble systemically active anthelmintics with other direct contact anthelmintics to obtain a relatively broad spectrum anthelmintic product.

We have found that it is possible to prepare a stable, relatively broad spectrum anthelmintic composition by choosing a vehicle which simultaneously provides systemic and direct contact availability for both systemic and direct contact anthelmintic drugs when in a carnivore gut. Details of the anthelmintic composition are described below.

SUMMARY OF THE INVENTION

We have found that the respective advantages of systemic and direct contact anthelmintics can be obtained in a single preparation with demonstrates broad spectrum anthelmintic efficacy in typical carnivores. In preferred embodiments this can be obtained by formulating both systemic and direct contact anthelmintic compounds into a single, aqueous, preferably paste-like formulation containing at least 50% by weight water. A typical anthelmintic paste effective against both common cestodes and common nematodes includes the anthelmintics febantel and praziquantel in a paste-like preparation having a tackiness which makes it difficult to spit out once placed into the mouth of a carnivore such as a dog or cat. In preferred embodiments the particle sizes of the febantel is closely controlled for efficacy such that at least 90% of the particle population has a particle size of less than 5 microns. To assure accurate delivery and dosage of the aqueous paste, especially if the paste is to be delivered via a paste syringe, the final combined paste product is deaerated prior to final packaging.

SPECIFIC EMBODIMENTS

A typical broad spectrum anthelmintic for dogs and cats using the principles of this disclosure is described below where the primarily systemically active anthelmintic is praziquantel and the primarily direct contact active anthelmintic is febantel. It should be understood, however, that it is thought that any combination of systemic and direct active compounds would be acceptable as long as they are compatible and can be carried in a vehicle which permits simultaneous systemic and direct contact activity when the preparation is in the gastrointestinal tract. Examples of the vehicles which would permit both systemic and direct contact activity include water, alcohols (e.g. ethanol, benzyl alcohol, glycols), oils (corn oil, peanut oil, sesame oil) and the like.

In the specific example below, the broad spectrum of parasites effectively eliminated, included the major nematode (hookworms—Ancylostoma sp. and *Uncinaria stepocephala,* whipworms—*Trichuris vulpis* and ascarids Toxocara sp. and *Toxascaris leonina*) and cestode (*Dipylidium caninum* and Taenia sp.) parasites.

Praziquantel has recently been shown to be 100% effective in the elimination of the cestode parasites in dogs and cats following an oral or injectable single dose administration using a logarithmic dosage schedule. It has also been shown that febantel was highly effective against nematodes but has limited activity against cestode parasites.

The anthelmintic activity of febantel must be primarily within the intestinal tract of the carnivore as the drug is poorly absorbed from that digestive system. Preliminary data also indicated that multiple doses in the carnivore were more effective than a single larger dose. A formulation would therefore need to maximize the time for direct contact within the intestinal tract. Preliminary trials with the drug in capsules and in suspension provided inconsistent response with various nematode parasites. A dose of 15 mg febantel/kg body weight or higher would be necessary to provide the desired consistent response.

The activity of praziquantel was demonstrated earlier to be primarily systemic as the drug was highly effective against cestodes when the drug was administered parenterally. The existing marketed forms of praziquantel utilize a single dose on a sliding scale such that the smaller dogs and cats should receive a minimum dose of up to 7.5 mg praziquantel/kg body weight and the larger animals as low as 3.5 mg/kg. The activity of multiple doses of praziquantel has previously been unknown.

THE PASTE FORMULATION

Unlike past anthelmintic preparations, our combination paste has an aqueous base and contains at least 50% by weight water. Although the key ingredients in our broad spectrum preparation are the systemic anthelmintic, the direct contact anthelmintic and a vehicle which assures the availability of both in the carnivore gut, other conventional ingredients such as thickeners, gelling agents, preservatives, flavoring agents and the like may be added.

Our representative combination anthelmintic paste formulation, added ingredients, and steps used to prepare the formulation, are given below.

TABLE I

| Ingredients | Percent (w/w) |
|---|---|
| 1. Febantel compound | 3.400* |
| 2. Praziquantel compound | 0.340* |
| 3. Acrylic acid polymer crosslinked with a polyalkenyl polyether (gelling agent)**** | 1.000 |
| 4. 1 Normal NaOH Solution** | 6.000 |
| 5. Distilled water*** | 53.400 |
| 6. Methyl Paraben (preservative) | 0.144 |
| 7. Propyl Paraben (preservative) | 0.024 |
| 8. Glycerine (solubilizing agent) | 10.000 |
| 9. Sorbitol 70% solution (flavoring agent) | 20.000 |
| 10. Polysorbate 80 (wetting agent) | 0.500 |
| 11. Distilled water*** | 5.192 |
| | 100.000 |

*100% Basis. Adjust for % purity and compensate with Item 5.
**The 1 Normal Sodium Hydroxide Solution is prepared by dissolving 4.0% w/v Sodium Hydroxide U.S.P. Pellets in distilled water.
***Hot distilled water (160° F. min). Cool to room temperature in an enclosed container before using. (Use immediately).
****Carbopol 934, B. F. Goodrich Co.

FORMULATION STEPS

Stock Solution (A) Charge Items 8 and 11 to a suitable stainless steel stock pot.

(B) Heat Items 8 and 11 to 50° C. while continually mixing.

(C) Continue mixing and add Items 6 and 7.

(D) Mix until Items 6 and 7 completely dissolve and a clear solution is obtained.

(E) Cool the solution to room temperature.

(F) Using distilled water (cooled to room temperature), QS the Stock solution to the theoretical weight.

(G) Mix well.

FINAL PRODUCT PREPARATION (A) Charge Item 5 to a double planetary mixing container.

(B) Start portable vertical mixer and slowly add Item 3.

(C) Mix until homogeneous.

(D) Remove the portable mixer and place the mixing container under the double planetary mixer. Continue mixing and add Item 4.

(E) Mix until a clear homogeneous gel is obtained.

(F) Quantitively transfer the "Stock Solution" into the mixer. Mix well.

(G) Add Item 9 and mix well.

(H) Continue mixing and add Item 10. Mix well.

(I) Add Item 2 and mix until Homogeneous.

(J) Add Item 1 and mix until Homogeneous.

(K) Pass the paste through a Comitrol Mill.

(L) Remix the paste. Deaerate if necessary.
(M) Deaerate the paste by remixing it under vacuum.
(N) Package.

COMBINATION PASTE ACTIVITY, PALATABILITY AND APPLICATION

In our best combination paste to date we have found that we can attain a high degree of consistency in anthelmintic activity at a dose of 10 mg febantel/kg body weight given once daily for three days; surprisingly, a minimum of a one-third lower dose than with previous efforts. Also with the paste combination, we have been able to reduce the total dose of praziquantel to 3 mg/kg (1 mg/kg daily for 3 days). For small dogs and cats, this praziquantel dose is, surprisingly, less than half what was previously established as the minimum effective dose. This is demonstrated below. Similar data have shown that the activity is the same in cats at the same dose as that demonstrated for dogs.

The combination paste formulation also is clearly easier to administer. The paste has a consistency such that it cannot easily be spit out once in the mouth. Palatability studies have shown that it is acceptable in the food to animals other than the very selective eating animals. Direct administration in clinical trials in cats, for example, demonstrated a clear superiority on ease of administration (89% acceptance) in comparison to the currently marketed positive control (63% acceptance of Vermiplex).

EFFICACY STUDIES

Ninety-four dogs were randomly assigned to 1 to 6 groups (5 treated and 1 untreated control) for the purpose of critical anthelmintic evaluation. Three anthelmintic formulations were studied: a febantel paste, a praziquantel paste and a combination paste containing both active ingredients. The treated animals were all dosed once daily for three days. The minimum effective dose of the combination paste was established at 10 mg febantel and 1.0 mg praziquantel/kg body weight (b.w.). At that dose 99.5–100% of all major nematode and cestode parasites identified (i.e., *Ancylostoma caninum, Trichuris vulpis, Toxocara canis, Dipylidium caninum* and *Taenia pisiformis*) were eliminated. Febantel paste alone was ineffective against cestodes (14.2% elimination of *D. caninum*) and praziquantel paste alone was ineffective (0–2.4% elimination) against the nematode parasites present.

The efficacy study had three objectives. The first was to titrate the minimum effective dose of a combination of febantel and praziquantel in dogs. The second was to reconfirm the lack of activity of praziquantel against nematodes, particulaly *T. vulpis,* and the lack of activity of febantel against cestodes, particularly *D. caninum.* And the third was to examine the effects of the combination against other naturally occurring nematode and cestode infections.

MATERIALS AND METHODS

Test Animals

The ninety-four random source dogs that were selected for this study were known carriers of naturally occurring nematode and/or cestode intestinal infections as established by fecal flotation and direct examinations. Initial emphasis was placed on identifying and using dogs infected with either *T. vulpis* or *D. caninum* or both. However, infections of *A. caninum, T. canis* and *T. pisiformis* were also studied. The dogs ranged in age from 6 months to 10 years and in weight from 7 to 68 pounds (3.2 to 30.8 kg) body weight (b.w.). There was a variety of mixed and purebred breeds including 45 males and 49 females.

The test animals were acclimated to their surroundings prior to being placed in the study. All were housed individually throughout the trial. They were given fresh water ad libitum and were fed once daily according to good husbandry practices. Following the determination of the intestinal parasitic infection the animals were randomly divided into 1 of 6 study groups (5 treated and 1 untreated control). This was done so that as many treated groups as possible including an untreated control were being studied in a single replicate.

TEST MEDICATIONS

Three paste formulations were utilized, each containing the same inert ingredients (Table II). One formulation contained febantel (Group E), one praziquantel (Group F) and the third the combination of febantel and praziquantel (Groups B, C and D). The individual doses were weighed, using an analytical balance, and placed in individual syringes. The dogs were dosed by extruding the paste onto the base of the dog's tongue. This same dose was administered once daily for 3 consecutive days. Food and water were not withheld before or after dosing.

TABLE II

| Study Group | Dosage and Administration | | |
|---|---|---|---|
| | Active Ingredient(s) | Daily Dose (mg/kg) | Number of Dogs Studied |
| A | None | Control | 16 |
| B | Febantel:Praziquantel | 5.0:0.5 | 18 |
| C | Febantel:Praziquantel | 10.0:1.0 | 30 |
| D | Febantel:Praziquantel | 15.0:1.5 | 20 |
| E | Febantel | 10.0 | 5 |
| F | Praziquantel | 1.0 | 5 |

Group A served as an untreated control. Groups B, C and D were studied to establish the minimum effective dose of the combination. Groups C, E and F were studied to determine the advantages of the combination over the individual drugs.

CRITICAL ANTHELMINTIC PROCEDURE

Each replicate studied contained at least 1 untreated control and 1 or more dogs in as many of the other groups as possible. One day prior to dosing the feces from each dog were collected, filtered through a No. 50 mesh screen and examined carefully for parasites. Any intestinal helminth observed was collected, identified as to genus and species when possible, counted and recorded. Following the initiation of treatment the same process of collecting the feces followed by identifying, counting and recording all parasites found in the feces was continued daily for 7 consecutive days. Parasites identified following treatment initiation were considered passed as a result of treatment.

Previous studies had shown cestodes were destroyed following dosing with praziquantel (see Kruckenberg et al, cited above). Scolex counts, the most frequently used method for counting tapeworms, have routinely been markedly lower in praziquantel treated animals than in untreated animals from the same source and studied at the same time. Therefore, in this study all fragments were collected and identified and counts for whole tapeworms were based on the counts of both scolicies and tapeworm necks with chains attached.

Dogs passing only nematode parasites were euthanatized and their intestinal tracts and all injesta were carefully examined 7 days after the initiation of dosing. Those with cestodes were studied similarly 14 days after dosing was initiated. All parasites recovered were identifed as to genus and species when possible, counted and the results recorded. The parasites remaining at necropsy were not considered affected by the drug.

The critical efficacy for each parasite species in each animal and in each group of animals was calculated according to the following formula:

$$\text{Critical efficacy} = \frac{\text{Number of parasites passed}}{\text{Number passed + number retained}} \times 100$$

EXAMPLE I (dogs)

No parasites were observed being passed before treatment in any of the dogs used in this study. A summary of the results of the parasites passed, those retained and the critical efficacy, is shown in Table III below. No intact parasites were passed by any of the 16 untreated control animals (Group A), though both Dipylidium and Taenia segments were observed prior to euthanasia. Overall there were 293 *A. caninum*, 104 *T. vulpis*, 98 *T. canis*, 180 *D. caninum* and 84 *T. pisiformis* recovered at necropsy in Group A.

Group B consisted of 18 dogs given 3 daily doses at 5 mg febantel and 0.5 mg praziquantel/kg b.w. In this group 80 of a total of 374 *A. caninum* were retained (294 passed) in the 11 dogs with this infection. Overall 78.6% of these parasites was passed. Other eliminations ranged from 99.5% of the *T. vulpis* and 98.9% of the *T. canis* to 81.8% of the *D. caninum*. Only the *T. pisiformis* in 2 dogs were completely (100%) eliminated.

A daily dose of 10 mg febantel and 1.0 mg praziquantel/kg b.w. for 3 days was given to the 30 dogs studied in Group C. In this group 5 of 1054 *A. caninum*, and 1 of 287 *T. canis*, were the only parasites retained. A minimum of 10 infections with each of the parasite species listed above were studied. Overall clearance ranged from 99.5% of the *A. caninum* and 99.7% *T. canis* to 100% of the *T. vulpis*, *D. caninum* and *T. pisiformis* identified. The response of this group was better overall than that of Group B.

The 20 dogs in Group D were treated with 15 mg febantel and 1.5 mg praziquantel/kg b.w. daily for 3 days. Three *A. caninum* of a total of 422 were retained (419 passed) for an overall clearance of 99.3% of these parasites. The other parasites present, i.e., *T. vulpis*, *T. canis*, *D. caninum* and *T. pisiformis* were all completely eliminated (100%) following treatment. There was very little difference in efficacy between Group C and Group D. The dose given to the dogs in Group C was the minimum effective dose.

The benefit of the combination was clearly demonstrated in comparing the results of Groups E and F with that of Group C. The dogs in Group E, receiving febantel paste, were completely (100%) cleared of the nematode infections, i.e., *A. caninum*, *T. vulpis*, and *T. canis*. However, only 14.2% of the *D. caninum* present were eliminated. By comparison, the 5 dogs in Group F were completely (100%) cleared of their cestode infections, i.e., *D. caninum* and *T. pisiformis*. The nematode infections in the dogs in Group F were nearly totally unaffected, i.e., 2.4% elimination of *A. caninum* and 0% elimination of *T. vulpis* and *T. canis*. The dogs in Group C, receiving in combination the same dose of the individual components in Groups E and F, effectively (99.5–100.0%) eliminated both nematodes and cestodes as described above. No adverse effects were observed in any of the treated animals.

Our preferred febantel/praziquantel paste formulation contains 34 mg febantel and 3.4 mg praziquantel/gram of paste and is designed to be administered at a rate of 1 gram of paste/7.5 lb (3.4 kg) body weight (b.w.).

Clinical evaluation indicated long-lasting effects as fecal flotations have been negative for as long as 28–30 days with a single three day dosage regimen.

TABLE III

Critical anthelmintic efficacy of febantel and praziquantel in dogs
Summary of Results

| Study Group | Avg. wt (lb) | Age range (yr) | Efficacy - total parasites passed/total retained - % | | | | |
|---|---|---|---|---|---|---|---|
| | | | A. caninum | T. vulpis | T. canis | D. caninum | T. pisiformis |
| A - Untreated Control | 29.4 (16) | 1–6 | 0/293(14)** 0% | 0/104(5) 0% | 0/98(5) 0% | 0/180(8) 0% | 0/84(5) 0% |
| B - Combination* (5:0.5 mg/kg) | 27.4 (18) | 1–10 | 294/80(11) 78.6% | 1092/5(10) 99.5% | 177+/2(6) 98.9% | 81/18(10) 81.8% | 5/0(2) 100% |
| C - Combination* (10:1 mg/kg) | 31.2 (30) | 0.5–7 | 1049/5(24) 99.5% | 407/0(10) 100% | 286+/1(11) 99.7% | 84/0(10) 100% | 363/0(10) 100% |
| D - Combination* (15:1.5 mg/kg) | 23.4 (20) | 0.5–6 | 419/3(14) 99.3% | 1024/0(10) 100% | 10+/0(2) 100% | 215/0(10) 100% | 42/0(2) 100% |
| E - Febantel (10 mg/kg) | 26.8 (5) | 1–4 | 140/0(4) 100% | 2/0(1) 100% | 10+/0(2) 100% | 25/151(5) 14.2% | — |
| F - Praziquantel (1 mg/kg) | 34.0 (5) | 2–3 | 10/404(4) 2.4% | 0/128(5) 0% | 0/57(1) 0% | 2/0(1) 100% | 2/0(1) 100% |

*Febantel:Praziquantel
† Includes immature parasites
**Numbers in parenthesis = number of animals

EXAMPLE II (cats)

In another study, 11 cats were dosed with febantel/praziquantel combination paste and 6 others were unmedicated controls, all studied by critical anthelmintic evaluation (which involves the sacrificing of animals to determine the number of parasites retained in the intestinal tract). The unmedicated cats basically maintained their infections, while the treated animals were cleared (100% elimination) of the *Ancylostoma tubaeforme, Toxocara cati,* and/or *Taenia taeniaeformis* infections present. Table IV summarizes these data.

TABLE IV

| | Febantel/Praziquantel Paste Administration to Cats | | | |
|---|---|---|---|---|
| | | | Efficacy-Total parasites passed/total retained - % | |
| Study Group | Avg. Wt. (lb.) | Age Range (yr.) | *Ancylostoma tubaeforme* | *Toxocara cati* | *Taenia taeniaeformis* |
| A - Untreated Control | 5.8 | 0.8->1 | 0/1 (2)* 0.0 | 0/27 (5) 0.0 | 0/22 (4) 0.0 |
| B - Combination (10:1 mg/kg) | 5.6 | 0.8->1 | 14/0 (2) 100 | 48/0 (10) 100 | 7.0 (7) 100 |

*Numbers in parenthesis = number of animals.

Given this disclosure, it is thought that variations will occur to those skilled in the art. Accordingly, it is intended that the scope of this invention should be limited only by the following claims.

We claim:

1. An oral anthelmintic composition for carnivores comprising effective amounts of a compound which is primarily systemically active and a compound which is primarily active via direct contact with helminths in a carnivore gut, the compounds being carried in a vehicle which simultaneously provides systemic and direct contact availability of the compounds, the composition being in the form of an aqueous paste containing at least 50% by weight water.

2. The composition of claim 1 wherein the systemically active anthelmintic is praziquantel and the anthelmintic having direct contact activity is febantel.

3. The composition of claim 1 wherein the respective amounts of the praziquantel and febantel, on a weight ratio, ranges from about 1:10 to 1:20.

4. The composition of claim 2 wherein the carnivore is a dog and the effective amount of praziquantel is about 1.0 mg/kg of canine body weight.

5. The composition of claim 2 wherein the carnivore is a dog and the effective amount of febantel is about 10.0 mg/kg of canine body weight.

6. The composition of claim 2 wherein the carnivore is a cat and the effective amount of praziquantel is about 1.0 mg/kg of feline body weight.

7. The composition of claim 2 wherein the carnivore is a cat and the effective amount of febantel is about 10.0 mg/kg of feline body weight.

8. The composition of claim 2 wherein the paste includes an acrylic acid polymer cross-linked with a polyalkenyl polyether.

9. The composition of claim 2 wherein the febantel is present in the form of particles having a closely controlled anthelmintically effective particle size such that at least 90% of the particle population has an average particle size less than about 5 microns.

10. An oral broad spectrum anthelmintic composition for dogs and cats comprising anthelmintically effective amounts of praziquantel and febantel in an aqueous, deaerated paste-like form and comprising at least 50% by weight water.

11. The composition of claim 10 wherein respective amounts of praziquantel and febantel, on a weight ratio, range from about 1:10 to 1:20.

12. The composition of claim 10 wherein the effective amount of praziquantel is about 1.0 mg/kg of dog or cat body weight.

13. The composition of claim 10 wherein the effective amount of febantel is about 10 mg/kg of dog or cat body weight.

14. The composition of claim 10 wherein the paste includes an acrylic acid polymer cross-linked with a polyalkenyl polyether.

15. The composition of claim 10 wherein the febantel is present in the form of particles having a closely controlled anthelmintically effective particle size such that at least 90% of the particle population has an average particle size of less than about 5 microns.

16. The composition of claim 12 wherein the paste-like form of the composition is such that it can be stored in and administered with an anthelmintic paste syringe.

* * * * *